United States Patent [19]

Guesdon et al.

[11] Patent Number: 5,776,693
[45] Date of Patent: Jul. 7, 1998

[54] SPECIFIC DETECTION OF THE MYCOBACTERIUM TUBERCULOSIS

[75] Inventors: Jean-Luc Guesdon, Sèvres; Dominique Thierry, Boulogne, both of France

[73] Assignee: Institut Pasteur, Paris, France

[21] Appl. No.: 461,773

[22] Filed: Jun. 5, 1995

Related U.S. Application Data

[63] Continuation of Ser. No. 983,552, filed as PCT/FR91/00457, Jun. 7, 1991 published as WO91/19004, Dec. 12, 1991, abandoned.

[30] Foreign Application Priority Data

Jun. 8, 1990 [FR] France ................... 90 07192

[51] Int. Cl.$^6$ .............. C12Q 1/68; C12P 19/34; C07H 21/04; C07H 21/02
[52] U.S. Cl. ............ 435/6; 435/91.2; 435/320.1; 536/23.1; 536/24.3; 536/24.32
[58] Field of Search ............ 435/6, 91.2, 320.1; 536/24.3, 24.32, 23.1

[56] References Cited

U.S. PATENT DOCUMENTS

| | | | |
|---|---|---|---|
| 4,489,159 | 12/1984 | Straus | 435/7 |
| 4,952,395 | 8/1990 | Shinnick et al. | 424/92 |

FOREIGN PATENT DOCUMENTS

| | | |
|---|---|---|
| 2651505 | 3/1991 | France . |
| 9010085 | 9/1990 | WIPO . |
| 9100085 | 1/1991 | WIPO . |
| 9119004 | 12/1991 | WIPO . |

OTHER PUBLICATIONS

Thierry et al. Nucleic Acids Research 18: 188–189, 1990.
Eisenach et al., J. Of infectious Diseases 161; 977–981, 1990.
Jouin et al. Infect. and Immunity 55(6): 1387–1392 (1987).
Langsley et al. Nucleic Acid Res. 13(11): 4191–4202 (1985).
Patel et al. J. of Clin. Microb. 28(3):513–518 (1990).
Thierry et al. Nucl. Acid Res 18(1): 188 (1989).
Reddi et al Int. Journal of Leprosy 36(4):592–598 (1988).
Eisenach et al. J. of Clin. Microb. 26(11):2240 (1988).
Eisenach et al. J.of Infec. Disease 161:977 (1990).
Altamisano et al. J of Clin. Microb. 30(8):2173 (1992).
Pao et al. Tubercle 69:27 (1988).
Pichen et al. Molec. of Cellular Probes. (2):111–124 (1988).
Pao et al. J. of Clin. Microb. 28(9): 1877 (1990).
Zainuddin et al. J. of Gen Microb. 3(1):29–34 (1989).

*Primary Examiner*—W. Gary Jones
*Assistant Examiner*—Dianne Rees
*Attorney, Agent, or Firm*—Burns, Doane, Swecker & Mathis, LLP

[57] ABSTRACT

The invention relates to a nucleic acid fragment derived from the *Mycobacterium tuberculosis* genome, characterized in that it contains one of the sequences I, II, III and IV, defined in the following manner:

I: a sequence chosen from one of the sequences A to H:
  A: 5'-CCCGCGGCAAAGCCCGCAGGACCA-CGATCG-3' (SEQ ID NO. 1)
  B: 5'-CGACCCGCCAGCCCAGGATCCTGCGAGCGT-3' (SEQ ID NO. 2)
  C: 5'-GGCGGGTCCAGATGGCTTGCTCGATCGCGT-3' (SEQ ID NO. 3)
  D: 5'-GTTGGCGGGTCCAGATGGCTTGCTCGATCG-3' (SEQ ID NO. 4)
  E: 5'-TCAAAGGGTTTGACAAATTAATGATTGGTC-3' (SEQ ID NO. 5)
  F: 5'-TCGTGTACAAAATGTGGACAAGTA-3' (SEQ ID NO. 6)
  G: 5'-TCGACGGACGTCGTGACCAGAAGTC-3' (SEQ ID NO. 7)
  H: 5'-GTCGACACGCCTTCTGCACGGGAAGTCCTT-3' (SEQ ID NO. 8)

II: a sequence containing at least 10 consecutive bases of one of the sequences A to F And having a total length of approximately 20 to 40 bases;
III: a sequence having a length of 20 to 40 bases which hybridizes with the sequence I or with the sequence II, and which preferably displays at least 80% homology with these sequences;
IV: a sequence complementary to one of the sequences I, II and III.

18 Claims, 11 Drawing Sheets

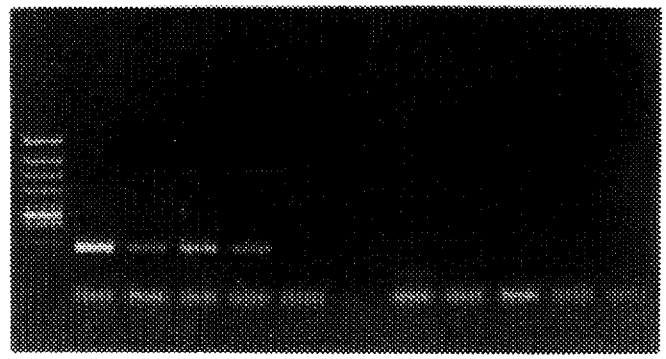
FIG. 1A
FIG. 1B
FIG. 2

```
          10         20         30         40         50         60
GTCGACACGC CTTCTGCACG GGAAGTCCTT CTGCGGCCAT CGTTGCTATG GCCGCTTACT
           H
          70         80         90        100        110        120
GCCTTCTAGT CCGTGCGGCT CTCGCAACAG CTCACGGGAC CTTTTTGAGG ATCGCCACTT
         130        140        150        160        170        180
CAGGTCTTCA ACTCGCGGAT GCCCTCATTG CAACGTTTG  CGCCTGCCT  TGGGGCGGCC
         190        200        210        220        230        240
GGCAGCCACC AAGTCGAGCA CTTTGCGGCG GAACTACTCG GGTAACACT  TCGGCACGGA
         250        260        270        280        290        300
CACGGCTCGT TCGACGGACG TCGTGACCAG AAGTCGAGCA AACCGACTCC ACTCTAGCTA
                        G
         310        320        330        340        350        360
GTGATACAAG CTTTTTTGTA GCCGCGCGAT GAACCGCCCC GGCATGTCCG GAGACTCCAG
         370        380        390        400        410        420
TTCTTGGAAA GGATGGGGTC ATGTCAGGTG GTTCATCGAG GAGGTACCCG CCGGAGCTGC
         430        440        450        460        470        480
GTGAGCGGGC GGTGCGGATG GTCGCAGAGA TCCGCGGTCA GCACGATTCG GAGTGGGCAG
         490        500        510        520        530        540
CGATCAGTGA GGTCGCCCGT CTACTTGGTG TTGGCTGCGC GGAGACGGTG CGTAAGTGGG
         550        560        570        580        590        600
TGCGCCAGGC GCAGGTCGAT GCCGGCGCAC GGCCCGGGAC CACGACCGAA GAATCCGCTG
         610        620        630        640        650        660
AGCTGAAGCG CTTAGCGGCG GGACAACGCC GAATTGCGAA GGGCGAACGC GATTTTAAAG
         670        680        690        700        710        720
ACCGCGTCGG CTTTCTTCGC GGCCGAGCTC GACCGGCCAG CACGCTAATT AACGGTTCAT
         730        740        750        760        770        780
CGCCGATCAT CAGGGCCACC GCGAGGGCCC CGATGGTTTG CGGTGGGGTG TCGAGTCGAT
         790        800        810        820        830        840
CTGCACACAG CTGACCGAGC TGGGTGTGCC GATCGCCCCA TCGACCTACT ACGACCACAT
```

FIG. 6A

```
              850        860        870        880        890        900
       CAACCGGGAG CCCAGCCGCC GCGAGCTGCG CGATGGCGAA CTCAAGGAGC ACATCAGCCG 910        920        930        940        950        960
       CGTCCACGCC GCCAACTACG GTGTTTACGG TGCCCGCAAA GTGTGGCTAA CCCTGAACCG 970        980        990       1000       1010       1020
       TGAGGGCATC GAGGTGGCCA GATGCACCGT CGAACGGCTG ATGACCAAAC TCGGCCTGTC 1030       1040       1050       1060       1070       1080
       CGGGACCACC CGCGGCAAAG CCCGCAGGAC CACGATCGCT GATCCGGCCA CAGCCCGTCC
                                     A
             1090       1100       1110       1120       1130       1140
       CGCCGATCTC GTCCAGCGCC GCTTCGGACC ACCAGCACCT AACCGGCTGT GGGTAGCAGA 1150       1160       1170       1180       1190       1200
       CCTCACCTAT GTGTCGACCT GGGCAGGGTT CGCCTACGTG GCCTTTGTCA CCGACGCCTA 1210       1220       1230       1240       1250       1260
       CGCTCGCAGG ATCCTGGGCT GGCGGGTCGC TTCCACGATG GCCACCTCCA TGGTCCTCGA
                              B
             1270       1280       1290       1300       1310       1320
       CGCGATCGAG CAAGCCATCT GGACCCGCCA ACAAGAAGGC GTACFCGACC TGAAAGACGT
       |           C                              |
             1330       1340   D  1350       1360       1370       1380
       TATCCACCAT ACGGATAGGG GATCTCAGTA CACATCGATC CGGTTCAGCG AGCGGCTCGC 1390       1400       1410       1420       1430       1440
       CGAGGCAGGC ATCCAACCGT CGGTCGGAGC GGTCGGAAGC TCCTATGACA ATGCACTAGC 1450       1460       1470       1480       1490       1500
       CGAGACGATC AACGGCCTAT ACAAGACCGA GCTGATCAAA CCCGGCAAGC CCTGGCGGTC 1510       1520       1530       1540       1550       1560
       CATCGAGGAT GTCGAGTTGG CCACCGCGCG CTGGGTCGAC TGGTTCAACC ATCGCCGCCT
```

FIG. 6B

```
              1570        1580        1590        1600        1610        1620
         CTACCAGTAC  TGCGGCGACG  TCCCGCCGGT  CGAACTCGAG  GCTGCCTACT  ACGCTCAACG 1630        1640        1650        1660        1670        1680
         CCAGAGACCA  GCCGCCGGCT  GAGGTCTCAG  ATCAGAGAGT  CTCCGGACTC  ACCGGGGCGG 1690        1700        1710        1720        1730        1740
         TTCACGATTG  GGCCGCCGTA  AGGAATGCGT  CATGAGCGAC  TTCGCATCAC  GGGCGACCAA 1750        1760        1770        1780        1790        1800
         TCATTAATTT  GTCAAACCCT  TTGAGATGCA  CTACTTGTCC  ACATTTGTA  CACGAAATAC
                          E                                F
              1810        1820        1830        1840        1850        1860
         CTAACACACT  ATGGTGCACA  TCACGCACTT  CCACGTTCCG  TATTCGGTGT  ACGATTTGTC 1870        1880
         ACGCAACTAA  GCGTTCAAGA  GGGAGT
```

```
                1610      1620      1630      1640      1650      1660      1670      1680      1690      1700
            GCTGCCTACGCTCAACGCCAGAGACCAGCCGCCGGCTGAGGTCTCAGATCAGAGAGTCTCCGGACTCACCGGGGCGGTTCACGATTGGGCCGCCGTA
            ^                       ^       ^ ^         ^               ^       ^ ^                ^^
            BBVI                    FNU4HI  DDEI MNLI   DDEI            HINFI HAPII HPHI           SAU96A
            FNU4HI                  NAEI    HAPII SAU3A                       ACCIII HAPII         HAEIII
                                    HAPII                                     HINFI NCII           FNU4HI
                                                                                    SCRFI 1710      1720      1730      1740      1750      1760      1770      1780      1790      1800
            AGGAATGCGTCATGAGCGACTTCGCATCACGGGCGACCAATCATTAATTGTCAAACCCTTTGAGATGCACTACTTGTCCACATTTGTACACGAAATAC
            ^    ^                                                        ^                       ^
            BSMI NLAIII               SFANI                                SFANI                   RSAI
            HGAI 1810      1820      1830      1840      1850      1860      1870      1880
            CTAACACACTATGGTGCACATCACGCACTTCCACGTTCCGTATTCGGTGTCACGCAACTAAGCCGTTCAAGAGGGAGT
            ^                                        ^       ^        ^       ^
            APALI                                    RSAI    MAEIII   DDEI    MNLI
            BSP1286
            HGIAI
```

FIG. 7E

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

CCCGCGGCAA AGCCCGCAGG ACCACGATCG                                30

(2) INFORMATION FOR SEQ ID NO:2:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

CGACCCGCCA GCCCAGGATC CTGCGAGCGT                                30

(2) INFORMATION FOR SEQ ID NO:3:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

GGCGGGTCCA GATGGCTTGC TCGATCGCGT                                30

(2) INFORMATION FOR SEQ ID NO:4:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

GTTGGCGGGT CCAGATGGCT TGCTCGATCG                                30

(2) INFORMATION FOR SEQ ID NO:5:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

TCAAAGGGTT TGACAAATTA ATGATTGGTC                                30

(2) INFORMATION FOR SEQ ID NO:6:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

TCGTGTACAA AATGTGGACA AGTA                                      24

(2) INFORMATION FOR SEQ ID NO:7:

(i) SEQUENCE CHARACTERISTICS:
    (A) LENGTH: 25 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:7:

TCGACGGACG TCGTGACCAG AAGTC 25

(2) INFORMATION FOR SEQ ID NO:8:

(i) SEQUENCE CHARACTERISTICS:
    (A) LENGTH: 30 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:8:

GTCGACACGC CTTCTGCACG GGAAGTCCTT 30

(2) INFORMATION FOR SEQ ID NO:9:

(i) SEQUENCE CHARACTERISTICS:
    (A) LENGTH: 30 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:9:

CTGATCCGGC CACAGCCCGT CCCGCCGATC 30

(2) INFORMATION FOR SEQ ID NO:10:

(i) SEQUENCE CHARACTERISTICS:
    (A) LENGTH: 30 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:10:

AGGCGTCGGT GACAAAGGCC ACGTAGGCGA 30

(2) INFORMATION FOR SEQ ID NO:11:

(i) SEQUENCE CHARACTERISTICS:
    (A) LENGTH: 30 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:11:

CGAGGACCAT GGAGGTGGCC ATCGTGGAAG 30

(2) INFORMATION FOR SEQ ID NO:12:

(i) SEQUENCE CHARACTERISTICS:
    (A) LENGTH: 30 base pairs
    (B) TYPE: nucleic acid
    (C) STRANDEDNESS: single ( D ) TOPOLOGY: linear ( i i ) MOLECULE TYPE: DNA (genomic)

( x i ) SEQUENCE DESCRIPTION: SEQ ID NO:12:

TGCCCTCATT GGCAACGTTT GCGCCCTGCC  30

( 2 ) INFORMATION FOR SEQ ID NO:13:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

CGTCGAGGAC CATGGAGGTG GCCATCGTGG  30

( 2 ) INFORMATION FOR SEQ ID NO:14:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

GACTTCTGGT CACGACGTCC GTCGAA  26

( 2 ) INFORMATION FOR SEQ ID NO:15:

( i ) SEQUENCE CHARACTERISTICS:
        ( A ) LENGTH: 1886 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

GTCGACACGC CTTCTGCACG GGAAGTCCTT CTGCGGCCAT CGTTGCTATG GCCGCTTACT  60

GCCTTCTAGT CCGTGCGGCT CTCGCAACAG CTCACGGGAC CTTTTGAGG ATCGCCACTT  120

CAGGTCTTCA ACTCGCGGAT GCCCTCATTG GCAACGTTTG CGCCCTGCCT TGGGGCGGCC  180

GGCAGCCACC AAGTCGAGCA CTTTGCGGCG GAACTACTCG GGTAACACT TCGGCACGGA  240

CACGGCTCGT TCGACGGACG TCGTGACCAG AAGTCGAGCA AACCGACTCC ACTCTAGCTA  300

GTGATACAAG CTTTTTTGTA GCCGCGCGAT GAACCGCCCC GGCATGTCCG GAGACTCCAG  360

TTCTTGGAAA GGATGGGGTC ATGTCAGGTG GTTCATCGAG GAGGTACCCG CCGGAGCTGC  420

GTGAGCGGGC GGTGCGGATG GTCGCAGAGA TCCGCGGTCA GCACGATTCG GAGTGGGCAG  480

CGATCAGTGA GGTCGCCCGT CTACTTGGTG TTGGCTGCGC GGAGACGGTG CGTAAGTGGG  540

TGCGCCAGGC GCAGGTCGAT GCCGGCGCAC GGCCCGGGAC CACGACCGAA GAATCCGCTG  600

AGCTGAAGCG CTTAGCGGCG GGACAACGCC GAATTGCGAA GGGCGAACGC GATTTTAAAG  660

ACCGCGTCGG CTTTCTTCGC GGCCGAGCTC GACCGGCCAG CACGCTAATT AACGGTTCAT  720

CGCCGATCAT CAGGGCCACC GCGAGGGCCC CGATGGTTTG CGGTGGGGTG TCGAGTCGAT  780

CTGCACACAG CTGACCGAGC TGGGTGTGCC GATCGCCCCA TCGACCTACT ACGACCACAT  840

CAACCGGGAG CCCAGCCGCC GCGAGCTGCG CGATGGCGAA CTCAAGGAGC ACATCAGCCG  900

-continued

| | | | | | | |
|---|---|---|---|---|---|---|
| CGTCCACGCC | GCCAACTACG | GTGTTTACGG | TGCCCGCAAA | GTGTGGCTAA | CCCTGAACCG | 960 |
| TGAGGGCATC | GAGGTGGCCA | GATGCACCGT | CGAACGGCTG | ATGACCAAAC | TCGGCCTGTC | 1020 |
| CGGGACCACC | CGCGGCAAAG | CCCGCAGGAC | CACGATCGCT | GATCCGGCCA | CAGCCCGTCC | 1080 |
| CGCCGATCTC | GTCCAGCGCC | GCTTCGGACC | ACCAGCACCT | AACCGGCTGT | GGGTAGCAGA | 1140 |
| CCTCACCTAT | GTGTCGACCT | GGGCAGGGTT | CGCCTACGTG | GCCTTTGTCA | CCGACGCCTA | 1200 |
| CGCTCGCAGG | ATCCTGGGCT | GGCGGGTCGC | TTCCACGATG | GCCACCTCCA | TGGTCCTCGA | 1260 |
| CGCGATCGAG | CAAGCCATCT | GGACCCGCCA | ACAAGAAGGC | GTACTCGACC | TGAAAGACGT | 1320 |
| TATCCACCAT | ACGGATAGGG | GATCTCAGTA | CACATCGATC | CGGTTCAGCG | AGCGGCTCGC | 1380 |
| CGAGGCAGGC | ATCCAACCGT | CGGTCGGAGC | GGTCGGAAGC | TCCTATGACA | ATGCACTAGC | 1440 |
| CGAGACGATC | AACGGCCTAT | ACAAGACCGA | GCTGATCAAA | CCCGGCAAGC | CCTGGCGGTC | 1500 |
| CATCGAGGAT | GTCGAGTTGG | CCACCGCGCG | CTGGGTCGAC | TGGTTCAACC | ATCGCCGCCT | 1560 |
| CTACCAGTAC | TGCGGCGACG | TCCCGCCGGT | CGAACTCGAG | GCTGCCTACT | ACGCTCAACG | 1620 |
| CCAGAGACCA | GCCGCCGGCT | GAGGTCTCAG | ATCAGAGAGT | CTCCGGACTC | ACCGGGCGG | 1680 |
| TTCACGATTG | GGCCGCCGTA | AGGAATGCGT | CATGAGCGAC | TTCGCATCAC | GGGCGACCAA | 1740 |
| TCATTAATTT | GTCAAACCCT | TTGAGATGCA | CTACTTGTCC | ACATTTGTA | CACGAAATAC | 1800 |
| CTAACACACT | ATGGTGCACA | TCACGCACTT | CCACGTTCCG | TATTCGGTGT | ACGATTTGTC | 1860 |
| ACGCAACTAA | GCGTTCAAGA | GGGAGT | | | | 1886 |

1
SPECIFIC DETECTION OF THE MYCOBACTERIUM TUBERCULOSIS

This application is a continuation of application Ser. No. 07/983,552, filed as PCT/FR91/00457, Jun. 7, 1991 published as WO91/19004, Dec. 12, 1991, now abandoned.

BACKGROUND OF THE INVENTION

1. Field of the Invention

The invention relates to a specific nucleic acid sequence of *Mycobacterium tuberculosis*, as well as to particular fragments of this sequence capable of playing the role of nucleic acid primers in the amplification of DNA originating from Mycobacterium in a biological sample. The invention also relates to a method for the detection of *Mycobacterium tuberculosis* in a biological sample, this method making use of the said nucleic acid primers.

The mycobacteria correspond to the genus Mycobacterium which comprises at least 54 different species.

Among the latter, about 10 are pathogenic or opportunistic pathogens for man or animals. *M. tuberculosis* is the agent responsible for tuberculosis.

2. Description of the Related Art Including Information Discussed Under 37 C.F.R. §§1.97–1.99

It is known that this disease represents a major problem for Public Health; in fact, there are at present between 15 and 60 million individuals suffering from tuberculosis in the world and 2 to 3 million people die each year as a result of this disease. In the developed countries, *M. tuberculosis* is the most common cause of mycobacterial infection. In France, about 10 new cases of tuberculosis appear each year. Vaccination by means of BCG (the Calmette-Guerin Bacillus, an attenuated strain of *M. bovis*) is far from being efficacious for all populations. This efficacy varies from about 80% in Western countries such as England to 0% in India (results of the last vaccination trial at Chingleput). Furthermore, the appearance of *M. tuberculosis* strains resistant to the usual antitubercular drugs and the existence of a correlation between tuberculosis and AIDS adds to the urgency of the need to develop a rapid method for the detection and identification of the mycobacteria.

For example, an epidemiological study carried out in Florida has shown that 10% of patients infected with AIDS were suffering from tuberculosis at the time when AIDS was diagnosed or 18 months before that. In 60% of these patients, tuberculosis appears in a disseminated form, hence not detectable by the standard diagnostic criteria such as pulmonary radiography or the analysis of sputum.

Finally, the diagnosis of tuberculosis and of other related mycobacterioses is difficult to carry out for various reasons: the pulmonary diseases caused by different mycobacteria cannot be clinically, radiologically or histologically distinguished; the mycobacteria are often present in small quantities and when they are present in quantities detectable by the methods classically used, the disease is already well developed and the patients present a risk of contagion to their close relatives; furthermore, on account of the very long generation time of these bacteria (24 h in the case of *M. tuberculosis* compared with 20 min for *E. coli*), the culture of these organisms is difficult. Thus 6 to 8 weeks are required to identify the microbes and even longer to obtain an antibiogram which can be used for adequate treatment of the patients. The need for a detection test not requiring the culture of the microbes and which can be used directly on pathological samples, even when the microbes are present in them in low concentrations, is thus essential.

Several procedures are presently used in the clinic to identify a mycobacterial infection.

First of all, the direct detection of the microorganism with the microscope should be mentioned: this procedure is rapid but does not permit the identification of the mycobacterial species observed and lacks sensitivity in as much as a large number of microorganisms must be present in the sample (>104/ml) for reliable detection (BATES J., CHEST, 1979, 76, (suppl.), 757–763).

When they are positive, the cultures have a specificity approaching 100% and permit the identification of the mycobacterial species isolated; nonetheless, as explained above, the growth of the mycobacteria in vitro requires from 3 to 6 weeks and when few mycobacteria are present at the site of the infection, repeated cultures are necessary in order to ensure a positive result (BATES J., 1979 and BATES J., et al., Am. Rev. Respir. Dis., 1986, 134, 415–417). The serological procedures may prove to be useful under certain conditions but their use is limited by their low sensitivity and/or their low specificity (DANIEL T. M. et al., Am. Rev. Respir. Dis., 1987, 135, 1137–1151).

The presence or absence of mycobacteria can also be determined by hybridization with DNA or RNA by using specific probes of the DNA sequences (KIEHN T. E. et al., J. Clin. Microbiol., 1987, 25, 1551–1552; ROBERTS M. C. et al., J. Clin. Microbiol., 1987, 25, 1239–1243; DRAKE T. A. et al., J. Clin. Microbiol., 1987, 25, 1442–1445). However, these methods are based on the polymorphism of the nucleotide sequences of the fragments used or on the polymorphism of the neighbouring regions and also require the culture of the microorganisms.

THIERRY et al. (Nucl. Acid Res., Vol. 18 No. 1, p. 188) have described a specific sequence from the *Mycobacterium tuberculosis* complex and designated it as IS 6110. The authors propose to use this sequence as a nucleotide probe for the detection of *Mycobacterium tuberculosis*. However, the amounts of mycobacterial DNA present in most of the biological samples are insufficient to give a positive signal; the hybridization technique using a nucleotide probe has thus been shown to be unsuitable for the identification of mycobacterial DNA extracted directly from biological samples.

In order to surmount this problem, some researchers have suggested amplifying specifically the DNA originating from the mycobacterium by using nucleotide primers in an amplification method such as the polymerase chain reaction (P.C.R.). PATEL et al. (J. Clin. Microbiol., Mar. 1990, 513–518) have described the use of several nucleotide primers selected from a sequence known to be a probe in the identification of *M. tuberculosis*. However, the length of the fragments obtained by using these primers was different from the expected theoretical length, and several fragments of variable size were obtained. Furthermore, the researchers observed no hybridization of the amplified products with the plasmid which was used to define the primers. These results indicate that these primers would not be suitable for the detection of the presence of *M. tuberculosis* in a biological sample and confirm the crucial nature of the choice of the primers.

SUMMARY OF THE INVENTION

The object of the present invention is to provide a method of detection of *M. tuberculosis* which is both specific, sensitive and reliable, and which does not require prior culture of the mycobacteria. The invention relates to a nucleic acid fragment derived from the genome of *Myco-* bacterium tuberculosis, characterized in that it includes one of the sequences I, II, III and IV, defined in the following manner:

I: a sequence |SEQ ID NOS: 1–8| selected from one of the sequences A to H:

A: 5'-CCCGCGGCAAAGCCCGCAGGACCACGAT-CG-3'

B: 5'-CGACCCGCCAGCCCAGGATCCTGCGAGCGT-3'

C: 5'-GGCGGGTCCAGATGGCTTGCTCGATCGCGT-3'

D: 5'-GTTGGCGGGTCCAGATGGCTTGCTCGATCG-3'

E: 5'-TCAAAGGGTTTGACAAATTAATGATTGGTC-3'

F: 5'-TCGTGTACAAAATGTGGACAAGTA-3'

G: 5'-TCGACGGACGTCGTGACCAGAAGTC-3'

H: 5'-GTCGACACGCCTTCTGCACGGGAAGTCCTT-3'

II: a sequence including at least 10 consecutive bases of one of the sequences A to H and having a total length of about 20 to 40 bases;

III: a sequence having a length of 20 to 40 bases which hybridizes with sequence I or with sequence II, and which preferably exhibits at least 80% homology with these latter;

IV: a sequence complementary to one of the sequences I, II or III.

The invention also relates to a couple of nucleic acid fragments derived from the genome of *Mycobaterium tuberculosis*, capable of playing the role of nucleotide primers in the amplification of the DNA originating from the said Mycobacterium in a biological sample, characterized in that it consists of two sequences selected from the sequences I to IV.

BRIEF DESCRIPTION OF THE DRAWINGS

FIG. 1A depicts a stained and electrophoresed agarose gel including multiple lanes corresponding to amplified DNAs of various bacterial species belonging to the genus Mycobacterium, one lane corresponding to a size marker and one lane corresponding to a TE buffer;

FIG. 1B depicts the results obtained by use of plasmid pMT02 as a probe on the amplified DNAs of various bacterial species belonging to the genus Mycobacterium;

FIG. 2 depicts a gel verifying the specificity of the primers with respect to DNA originating from *E. coli* or human cells;

FIG. 6 depicts the complete sequence including the primers A to H; and

Figure 7A:
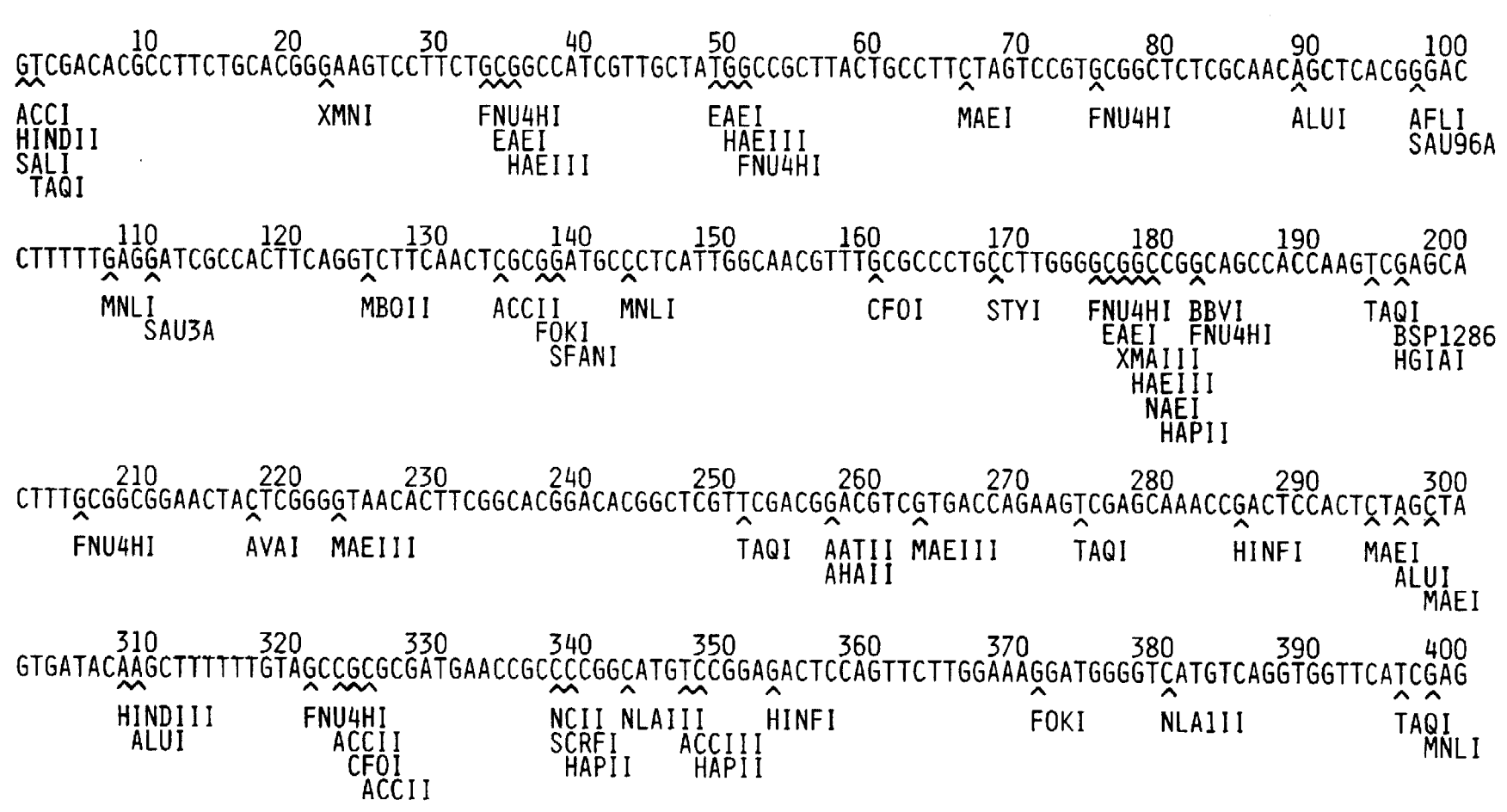
Figure 7B:
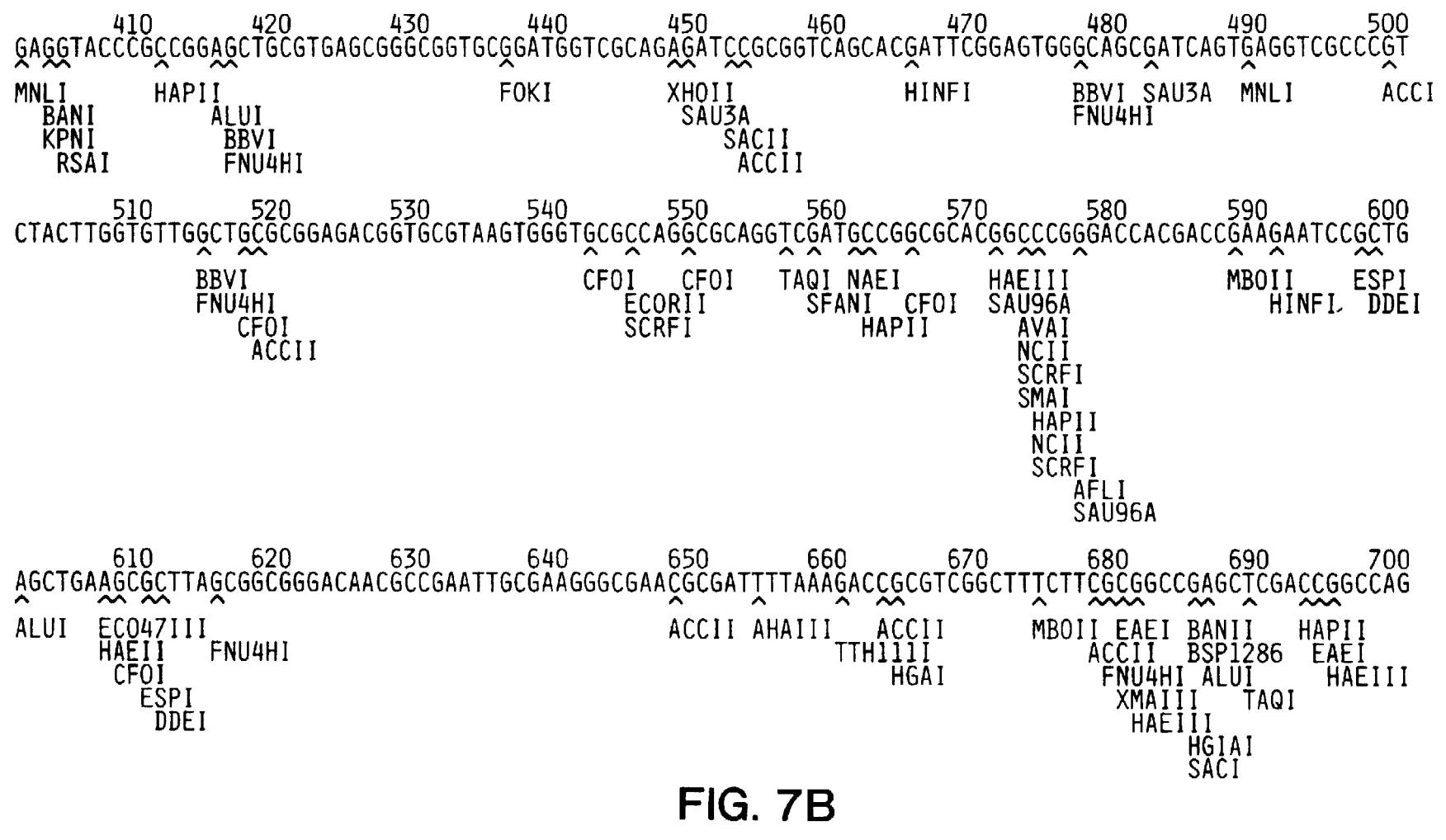
Figure 7D:
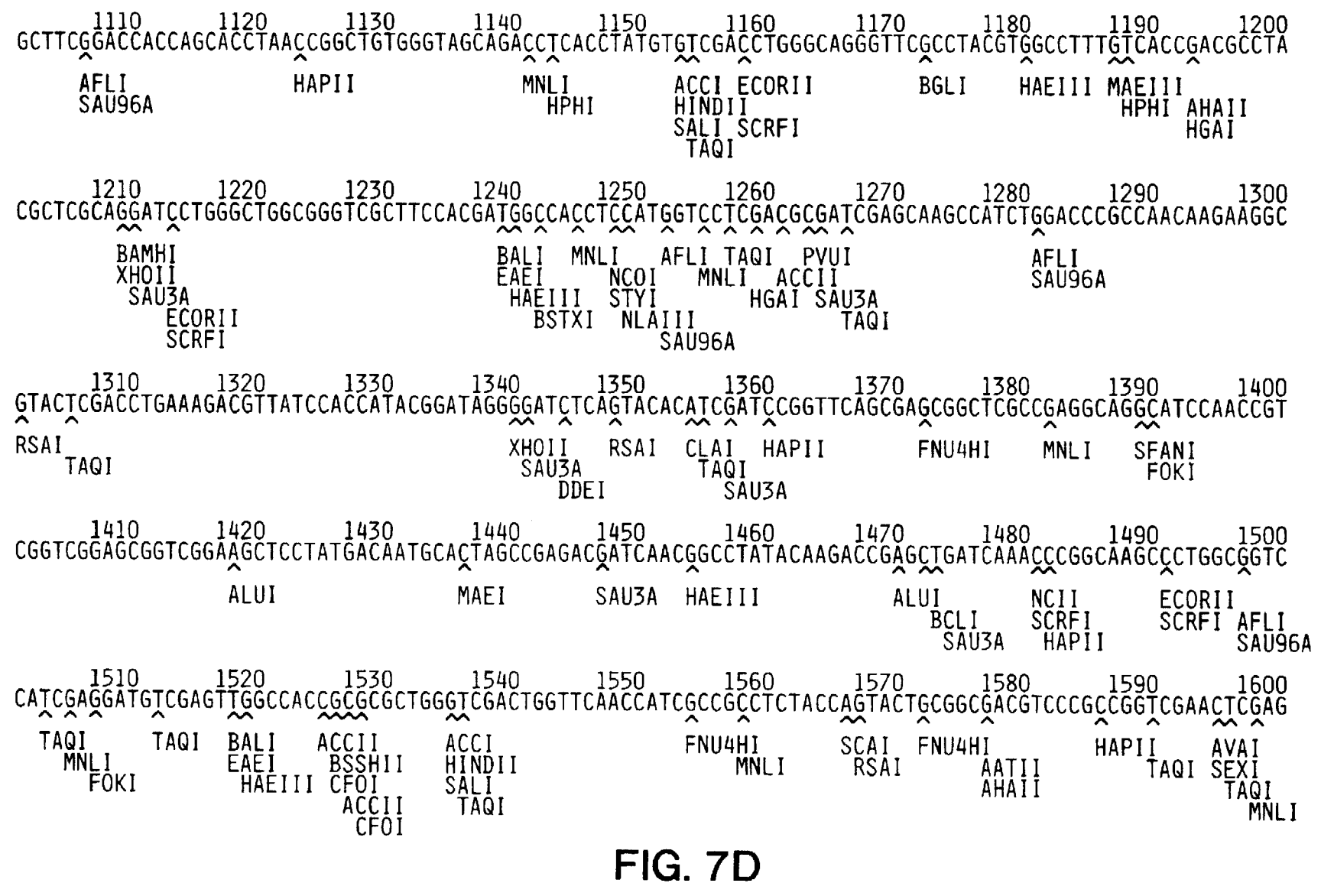

FIG. 7 depicts the restriction map of the sequence shown in FIG. 6.

DESCRIPTION OF THE PREFERRED EMBODIMENTS

Figure 3:
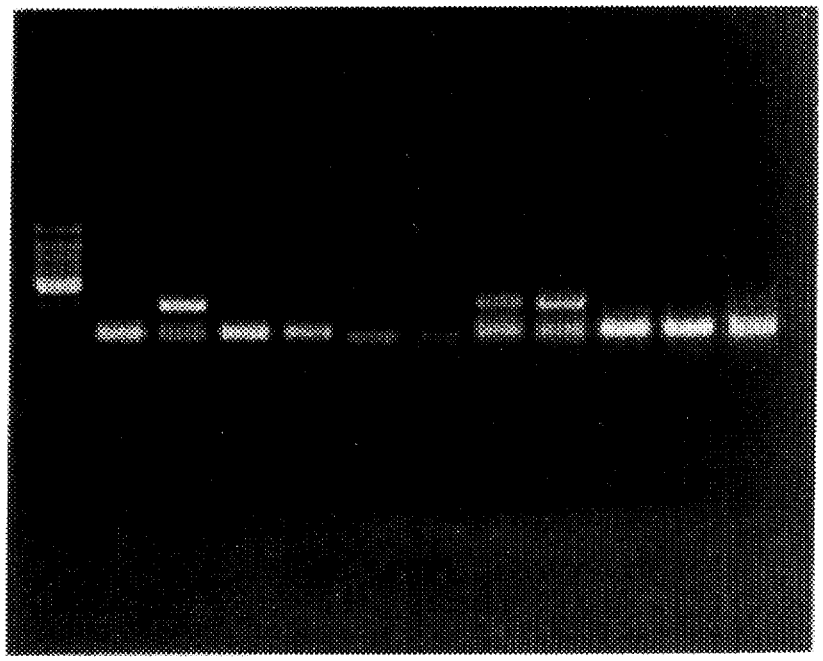
FIG. 3 depicts the results of an agarose gel analysis after PCR on biological samples obtained from 11 different persons.

The inventors have identified this series of nucleic acid fragments capable of playing the role of primers starting from the sequence IS 6110 (Nucl. Acid. Res. Vol 18 No. 1, 1990) and sequences which are next to the sequence IS 6110 in the genome of *M. tuberculosis*. These latter have been identified in the framework of this invention by the inventors. The sequence IS 6110 described in Nucl. Acid. Res., Vol. 18 No. 1, 1990 forms part of the sequence shown in FIG. 6. More particularly, the sequence IS 6110 extends from base 327 to base 1687 of the sequence shown in FIG. 6.

The primers of the invention exhibit characteristics essential for their use in the selective amplification of DNA from *M. tuberculosis*, namely the absence of homology with the human genome and the absence of amplification of related sequences likely to be present in the biological sample (for example the *E. coli* sequence IS 3411). Furthermore, the inventors have observed that the results obtained by using the primers of the invention are very reliable in as much as the length of the fragments obtained corresponds to the expected, theoretical length and are a constant length which does not vary. This is true even for the primer couples which lead to the amplification of very long fragments (of the order of 1000 to 1500 bases) where the risk of interruption of the polymerization is very high on account of the effects of the secondary structure of the sequence. Furthermore, a check of the amplification products by means of hybridization with a nucleotide probe containing the sequence shown in FIG. 6 or a fragment of this sequence confirms the reliability of the method. These results could not have been foreseen. Starting from the sequence IS 6110, it would be possible to prepare a large number of nucleotide primers, but few of them would be efficient and/or specific.

FIG. 6 illustrates the positions of the primers A to H with respect to the entire sequence.

FIG. 7 shows the restriction map of the sequence shown in FIG. 6.

According to an embodiment of the invention, the primer couple is selected from the sequences I to IV such that the product of amplification has a length of between 100 and 300 nucleotides, for example between about 100 and 200 nucleotides. Couples in which the positive primer is constituted of the sequence A and the negative primer is constituted of one of the sequences B, C and D, are particularly preferred. Another particularly preferred primer couple is that in which the positive primer is constituted of the sequence H and the negative primer is constituted of the sequence complementary to the sequence G.

The primers of the invention can also be constituted of a sequence II which has a length of 20 to 40 bases and which includes at least 10 consecutive bases of one of the sequences A to H. As an example of this type of primer, mention may be made of fragments of one of the sequences A to H having between 20 to 30 bases and also of one of the sequences A to H to which linkers have been added, for example a EcoRI linker, GAAT. It is particularly preferred to use primers in which the first 5 nucleotides at the 3' end are 100% homologous to those present in the corresponding part of the sequence to be amplified. It is also possible to use as primer a sequence III having a length of 20 to 40 bases which hybridizes under stringent conditions with the sequence I or II. This type of sequence usually exhibits at least 80% homology with the sequence with which it hybridizes. In this manner, it is possible to replace some bases of the sequences A to H with other bases or to add bases to the ends of the sequences A to H. The stringent conditions are those normally used in the art.

The invention also relates to sequences IV which are sequences complementary to one of the sequences I, II or III, for example complementary to one of the sequences A to H.

The invention also relates to a method for the detection of the presence of *Mycobacterium tuberculosis* in a biological sample, characterized by the following steps:

i) the placing of the biological sample in contact with a couple of nucleic acid fragments, so-called primers, according to the invention, the DNA contained in the sample having been, if necessary, made accessible to hybridization beforehand and under conditions leading to hybridization of the primers with the DNA of *Mycobacterium tuberculosis*;

ii) amplification of the DNA of *Mycobaterium tuberculosis*;

iii) detection of the amplification of DNA fragments corresponding to the fragment flanked by the primers, for example by means of gel electrophoresis;

iv) confirmation, if necessary, of the sequence of the amplified fragment, for example, by means of hybridization with a specific probe, by sequencing or by analysis of restriction sites. The biological sample may be any sample likely to contain *M. tuberculosis*, for example sputum, urine, blood. Usually, the samples are subjected to a treatment in order to extract the DNA and to make it accessible to hybridization. These treatments are known to the art. The conditions used for the amplification are the following:

| 1st cycle | i) about 94° C. 5 minutes<br>ii) about 60° C. 1 minute | 1 X |
|---|---|---|
| subsequent cycles | i) about 94° C. 15 seconds<br>ii) about 60° C. 1 minute | 20 to 40 X |
| last cycle | i) about 94° C. 15 seconds<br>ii) about 60° C. 5 minutes | 1 X |

The demonstration that amplification has occurred may be performed by means of gel electrophoresis, for example on an agarose gel stained with ethidium bromide. After having carried out the amplification it is possible, in the framework of the invention, to verify the sequence of the amplified fragment, for example by means of hybridization with a nucleotide probe, the said probe comprising at least a part of the sequence. Such probes are the plasmids pMT01, containing the bases 1 to 1152 of the sequence shown in FIG. 6 and the plasmid pMT02, containing the bases 309 to 1219 of the said sequence. Other suitable probes would be any probe having a length of at least 20 bases, capable of hybridizing under stringent conditions with a part of the sequence IS 6110 situated between the two primers selected. Particularly preferred probes are the following sequences J, K, L, M:

J: 5'-CTGATCCGGCCACAGCCCGTCCCGCCGATC-3'(SEQ ID NO: 9)

K: 5'-AGGCGTCGGTGACAAAGGCCACGTAGGCG-A-3'(SEQ ID NO: 10)

L: 5'-CGAGGACCATGGAGGTGGCCATCGTGGA-AG-3'(SEQ ID NO: 11)

M: 5'-TGCCCTCATTGGCAACGTTTGCGCCCTGCC-3'(SEQ ID NO: 12)

The hybridization conditions used for such a check might be the following:

| hybridization: about 65 to 68° C. | 6 × SSC<br>10% dextran sulfate<br>5 × Denhardt's<br>10 mM EDTA<br>0.5% SDS<br>100 μg/ml of salmon sperm DNA |
|---|---|
| washing: about 65° C. | 2 × SSC (twice for 10 min)<br>2 × SSC + 0.1% SDS<br>(once for 30 mn)<br>0.1 × SSC (once for 10 min) |

1×SSC corresponds to 0.15M NaCl and 0.05M Na citrate and a 1×Denhardt's solution corresponds to 0.02% Ficoll, 0.02% polyvinylpyrrolidone and 0.02% bovine serum albumin.

Other means to check the identity of the amplification products consists in the direct sequencing of the fragment or in an analysis of restriction sites. However, this check is not an obligatory step of the method, since the primers of the invention lead to very faithful amplification of the sequence.

It is to be noted that the amplification according to the invention is specific for the DNA of the *Mycobacterium tuberculosis* complex (see, for example FIGS. 1A and 1B). The amplification observed with the DNA of *M. bovis-BCG, M. bovis* and *M. microti* does not lessen the usefulness of the method in as much as these mycobacteria are not likely to be present in a sample of human origin. *M. bovis* is responsible for tuberculosis in cattle and *M. microti* is the causal agent of tuberculosis in rodents. The primers of the invention do not lead to any amplification of DNA originating from other types of Mycobacteria such as *M. fortiutum, M. gordonae, M. avium,* etc.

Furthermore, the primers of the invention do not amplify DNA of human or bacterial origin (for example *E. coli*). This is illustrated in FIG. 2.

The invention also relates to a kit for the detection of the presence of *Mycobacterium tuberculosis* in a biological sample, characterized in that it contains the following elements:

a couple of nucleic acid fragments according to any one of the claims 1 to 5;

the reagents necessary to carry out an amplification of DNA;

possibly a component making it possible to check the sequence of the amplified fragment, more particularly a nucleotide probe according to any one of the claims 8 to 10.

The invention also relates to the entire sequence shown in FIG. 6. The inventors have observed that this sequence contains two open reading frames, one of which resembles a gene coding for a transposase.

The invention will be illustrated by the following non-limiting examples.

EXAMPLES

Example 1 selection and synthesis of the oligonucleotide primer couples.

Starting from the complete sequence illustrated in FIG. 6, several oligonucleotide primer couples were selected and synthesized. These primer couples are illustrated below. For some of these primer couples, the sequences of the oligonucleotide probes likely to be used to detect the amplification products are indicated:

Primer Couple No. 1 positive primer [SEQ ID NO: 1]:
5'-CCCGCGGCAAAGCCCGCAGGACCACGATCG-3' negative primer [SEQ ID NO: 2]:
5'-CGACCCGCCAGCCCAGGATCCTGCGAGCGT-3'
length of the amplified fragment excluding primers: 141
probes for the primer couple No. 1

[SEQ ID NO: 9] 1) 5'-CTGATCCGGCCA-CAGCCCGTCCCGCCGATC-3'

[SEQ ID NO: 10] 2) 5'-AGGCGTCGGTGAC-AAAGGCCACGTAGGCGA-3'

Primer Couple No. 2 positive primer [SEQ ID NO: 1]:
5'-CCCGCGGCAAAGCCCGCAGGACCACGATCG-3'
negative primer [SEQ ID NO: 3]:
5'-GGCGGGTCCAGATGGCTTGCTCGATCGCGT-3'
length of the amplified fragment excluding primers: 201
probes for the primer couple No. 2

[SEQ ID NO: 9] 1) 5'-CTGATCCGGCCAC-AGCCCGTCCCGCCGATC-3'

[SEQ ID NO: 11] 2) 5'-CGAGGACCATGG-AGGTGGCCATCGTGGAAG-3'

Primer Couple No. 3 positive primer [SEQ ID NO: 1]:
5'-CCCGCGGCAAAGCCCGCAGGACCACGATCG-3'
negative primer [SEQ ID NO: 4]:
5'-GTTGGCGGGTCCAGATGGCTTGCTCGATCG-3'
length of the amplified fragment excluding primers : 204
probes for the primer couple No. 3

[SEQ ID NO: 9] 1) 5'-CTGATCCGGCC-ACAGCCCGTCCCGCCGATC-3'

[SEQ ID NO: 13] 2) 5'-CGTCGAGGACC-ATGGAGGTGGCCATCGTGG-3'

Primer Couple No. 4 positive primer [SEQ ID NO: 1]:
5'-CCCGCGGCAAAGCCCGCAGGACCACGATCG-3'
negative primer [SEQ ID NO: 5]:
5'-TCAAAGGGTTTGACAAATTAATGATTGGTC-3'
length of the amplified fragment excluding primers 740

Primer Couple No. 5 positive primer [SEQ ID NO: 1]:
5'-CCCGCGGCAAAGCCCGCAGGACCACGATCG-3'
negative primer [SEQ ID NO: 6]:
5'-TCGTGTACAAAATGTGGACAAGTA-3'
length of the amplified fragment excluding primers: 770

Primer Couple No. 6 positive primer [SEQ ID NO: 7]:
5'-ICGACGGACGTCGTGACCAGAAGTC-3'
negative primer [SEQ ID NO: 2]:
5'-CGACCCGCCAGCCCAGGATCCTGCGAGCGT-3'
length of the amplified fragment excluding primers : 980

Primer Couple No. 7 positive primer [SEQ ID NO: 7]:
5'-TCGACGGACGTCGTGACCAGAAGTC-3'
negative primer [SEQ ID NO: 3]:
5'-GGCGGGTCCAGATGGCTTGCTCGATCGCGT-3'
length of the amplified fragment excluding primers: 1040

Primer Couple No. 8 positive primer [SEQ ID NO: 7]:
5'-ICGACGGACGTCGTGACCAGAAGTC-3' negative primer [SEQ ID NO: 6]:
5'-TCGTGTACAAAATGTGGACAAGTA-3'
length of the amplified fragment excluding primers : 1550

Primer Couple No. 9 positive primer [SEQ ID NO: 8]:
5'-GTCGACACGCCTTCTGCACGGGAAGTCCTT-3'
negative primer [SEQ ID NO: 14]:
5'-GACTTCTGGTCACGACGTCCGTCGAA-3'
length of the amplified fragment excluding primers : 219
probe for the primer [SEQ ID NO: 12] couple No. 9
5'-TGCCCTCATTGGCAACGTTTGCGCCCTGCC-3'

Example 2 verification of the specificity of the primers with respect to other types of Mycobacteria The specificity of the primers was verified by using the DNA of various bacterial species belonging to the genus Mycobacterium.

The total DNA isolated from samples of different types of Mycobacteria is subjected to amplification by means of the "Polymerase Chain Reaction" (P.C.R.) procedure by using the primer couple No. 1 mentioned in Example 1.

The parameters of the P.C.R. steps were selected in the following manner:

| 1st cycle | i) about 94° C. 5 minutes<br>ii) about 60° C. 1 minute | 1 X |
|---|---|---|
| subsequent cycles | i) about 94° C. 15 seconds<br>ii) about 60° C. 1 minute | 20 to 40 X |
| last cycle | i) about 94° C. 15 seconds<br>ii) about 60° C. 5 minutes | 1 X |

The products of amplification are analysed by means of electrophoresis on agarose gel and staining with ethidium bromide.

FIG. 1A shows the results. The lanes indicated in FIG. 1A correspond to the following samples:

| | |
|---|---|
| 1 Size markers | 7 M. gordonae |
| 2 Mycobacterium tuberculosis | 8 M. intracellularae |
| 3 M. bovis-BCG | 9 M. paratuberculosis |
| 4 M. bovis | 10 M. scrofulaceum |
| 5 M. microti | 11 M. avium |
| 6 M. fortiutum | 12 TE buffer |

FIG. 1B shows the results obtained when the plasmid pMT02 (labelled by means of the AAF according to Kourilsky et al., French patent application 8124131) was used as probe on the amplification products obtained in this example. The construction of the plasmid pMT02 is described in Example 6.

Example 3 verification of the specificity of the primers with respect to DNA originating from Escherichia Coli or human cells.

Human DNA may contaminate the samples to be analysed. The amplification procedure described in Example 2 is applied to samples of total DNA in the presence of the primer couple No. 1.

The amplification products are analysed by means of electrophoresis on agarose gel and staining with ethidium bromide. FIG. 2 shows the results. the different lanes corresponding to the following samples:

1-*Mycobaterium tuberculosis*
2-Human DNA
3-*Mycobacterium tuberculosis*+human DNA
4-DNA of *Escherichia coli*
5-TE buffer

Example 4
use of the probes on DNAs present in biological samples

10 μl of amplified samples taken from the sputum of patients with tuberculosis are loaded onto a 2% agarose gel in TAE buffer (0.04M Tris-acetate, 0.001M EDTA) and 1 pg/ml EtBr. The amplification is performed by means of the polymerase chain reaction (P.C.R.) procedure according to Saiki et al. (Science 1988, 239, 487–491) by using 12.5 pmoles of oligonucleotides (primer couple No. 1) and the DNA of biological samples with 2 U of Taq polymerase in a buffer 50 mM KCl, 10 mM Tris HCl, pH 8.3, 2.4 mM MgCl$_2$, 300 μM of deoxyribonucleotides and 100 μg/ml of gelatin. The final volume of the reaction mixture is 100 μl. The parameters of the P.C.R. steps were selected in the following manner: 1 mn at 94° C., 1 mn at 50° C., 1 mn at 72° C. for 40 cycles.

FIG. 3 shows the results of the analysis on agarose gel after P.C.R. of these samples. The lanes 1 to 11 correspond to biological samples obtained from 11 different persons. These results were verified by direct reading in the microscope and confirmed the results obtained by amplification:

negative biological samples by direct reading : lanes 1–3–4–5–6–9–10;

positive biological samples by direct reading : lanes 2–7–8–11;

the amplified bands are visualized under UV.

Example 5
analysis on agarose gel of *M. tuberculosis* DNA amplified with different oligonucleotide primer couples.

10 μl of the amplified samples are loaded onto a 2% agarose gel. The amplification is performed according to the procedure already described by using several primer couples described in Example 1.

Figure 4:
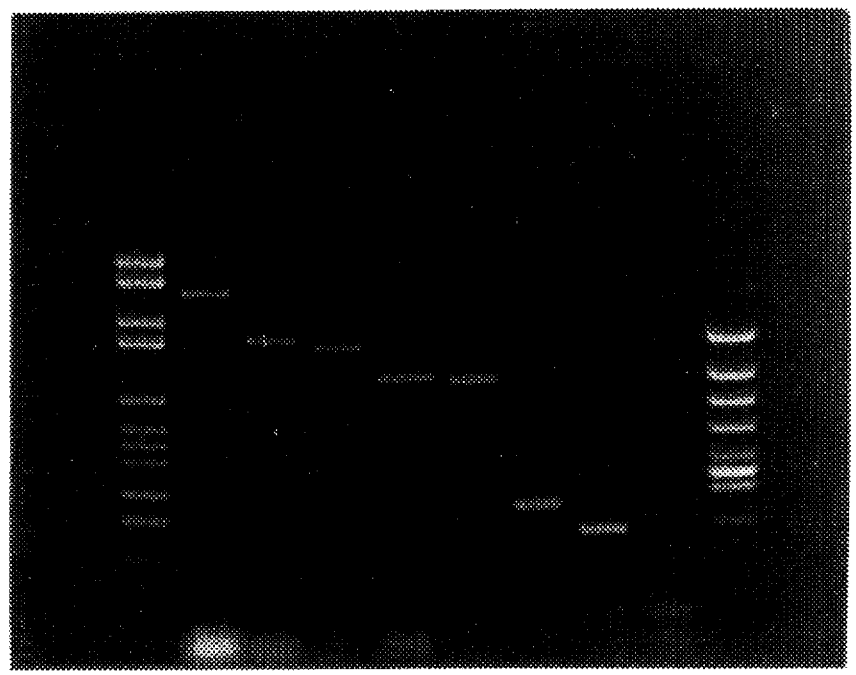
FIG. 4 depicts an agarose gel of *M. tuberculosis* DNA amplified with different oligonucleotide primer couples.

FIG. 4 shows these results:

|  |  |
|---|---|
| lane 1: | primer couple No. 8 |
| lane 2: | primer couple No. 7 |
| lane 3: | primer couple No. 6 |
| lane 4: | primer couple No. 5 |
| lane 5: | primer couple No. 4 |

| | |
|---|---|
| lane 6: | primer couple No. 2 |
| lane 7: | primer couple No. 1 |
| lane 8: | negative control |

M=marker

The amplified bands are visualized under UV.

These results confirm that the amplified fragments are of a length corresponding to the theoretical length, calculated from the distance between each primer. It is surprising that in spite of the use of some primer couples leading to the amplification of very long fragments, no interruption of the polymerization resulting from a secondary structure of the sequence is observed.

The results were verified by hybridization with the plasmid pMT01 (CNCM I-900 deposited on Aug. 25, 1989) which contains the bases 1 to 1152 of the sequence illustrated in FIG. 6.

Example 6
construction of the plasmid pMT02

The plasmid pMT02 was constructed by cloning a Hind III/Bam HI fragment of 900 base pairs derived from the sequence IS 6110 into the vector pUC18 (fragment which corresponds to the bases 309 to 1219 of the sequence illustrated in FIG. 6).

The plasmid pMT02 can serve as probe for the verification of the amplified sequences. The specificity of pMT02 was determined by Southern blot after complete digestion of various mycobacterial DNAs by means of Bam HI.

Figure 5:
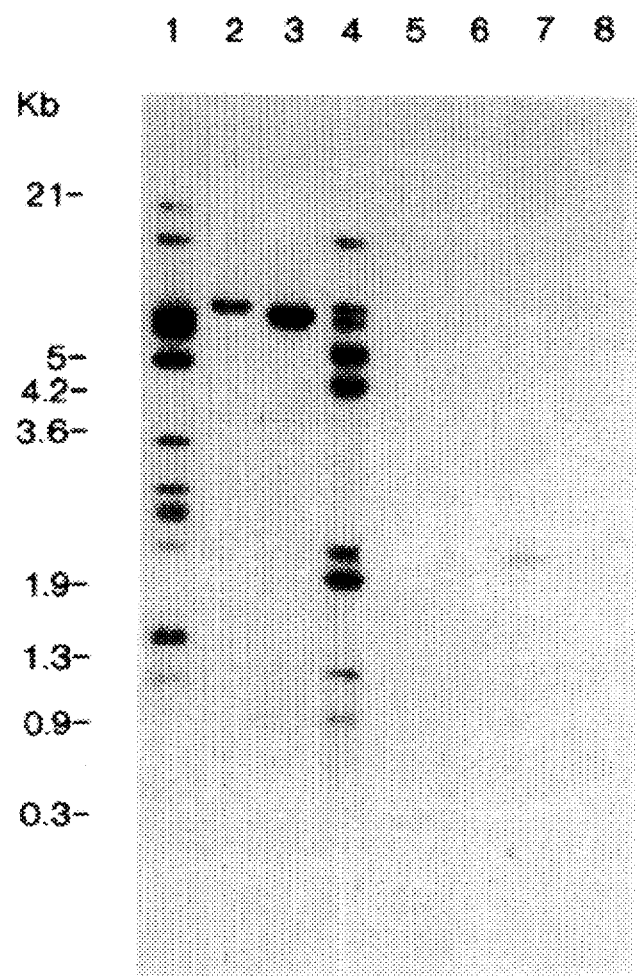
FIG. 5 depicts a Southern blot demonstrating the specificity of plasmid pMT02 as a probe for verification of various amplified and digested mycobacterial DNAs.

The results are shown in FIG. 5.

The different lanes shown in FIG. 5 have the following meanings:

| | |
|---|---|
| 1 *M. tuberculosis* \ 2 *M. bovis*-BCG \ 3 *M. bovis* \ 4 *M. microti* / | tuberculosis complex |
| 5 *M. paratuberculosis* \ 6 *M. intracellularae* \ 7 *M. scrofulaceum* \ 8 *M. avium* / | avium complex |

---

We claim:

1. Isolated nucleic acid fragment comprising a sequence I, II, III or IV wherein I is a sequence selected from the group consisting of one of the sequences A to H:

A: 5'-CCCGCGGCAAAGCCCGCAGGACCAC-GATCG-3' SEQ ID NO: 1
B: 5'-CGACCCGCCAGCCCAGGATCCTGCGAGCGT-3' SEQ ID NO: 2
C: 5'-GGCGGGTCCAGATGGCTTGCTCGATCGCGT-3' SEQ ID NO: 3
D: 5'-GTTGGCGGGTCCAGATGGCTTGCTCGATCG-3' SEQ ID NO: 4
E: 5'-TCAAAGGGTTTGACAAATTMTGATTGGTC-3' SEQ ID NO: 5
F: 5'-TCGTGTACAAAATGTGGACMGTA-3' SEQ ID NO: 6
G: 5'-TCGACGGACGTCGTGACCAGAAGTC-3' SEQ ID NO: 7
H: 5'-GTCGACACGCCTTCTGCACGGGMGTCCTT-3' SEQ ID NO: 8

II is a sequence including at least 10 consecutive bases of one of the sequences A, C, D, E, F, G and H and consisting of a total length of about 20 to 40 bases;

III is a sequence consisting of a length of 20 to 40 bases which specifically hybridizes under highly stringent conditions, with sequence I or with sequence II at a hybridization region within sequence I or sequence II; and IV is a sequence fully complementary to one of the sequences I, II or III.

2. Isolated nucleic acid fragments which are nucleotide primers in the amplification of the DNA of *Mycobacterium tuberculosis* in a biological sample comprising two sequences of at least 10 consecutive bases selected from the sequences I to IV according to claim 1.

3. Nucleic acid fragments according to claim 2 wherein at least one of the two sequences is sequence I.

4. Nucleic acid fragments according to claim 2 or 3 comprising one of the sequences A or G and one of the sequences B, C, D, E, F or also the sequence H and the sequence fully complementary to the sequence G.

5. Nucleic acid fragments according to claim 4 comprising the sequence A and one of the sequences B, C, D.

6. Method for the detection of the presence of *Mycobacterium tuberculosis* in a biological sample comprising the steps of:

i) placing the biological sample in contact with two nucleic acid fragments according to claim 1;
ii) amplifying the DNA of *Mycobacterium tuberculosis* using said nucleic acid fragments as primers; and
iii) detecting the amplified DNA fragments corresponding to the fragment flanked by the primers.

7. Method for the detection of the presence of *Mycobacterium tuberculosis* according to claim 6, wherein the DNA is amplified according to a process comprising the following cycles:

a first cycle wherein the DNA to amplify is incubated at about 94° C. during 5 minutes and then at about 60° C. during 1 minute;
20 to 40 cycles wherein the DNA, obtained after the first cycle, is incubated at about 94° C. during 15 seconds and then at about 60° C. during 1 minute; and
a last cycle wherein the DNA, obtained after the 20 to 40 cycles, is incubated at about 94° C. during 15 seconds and then at about 60° C. during 5 minutes.

8. Nucleotide probe hybridizing with the amplification products obtained at step ii) of the method according to claim 6, wherein said nucleotide probe comprises a sequence of at least 20 bases in length and is capable of hybridizing under highly stringent conditions with the part of the sequence IS 6110 located between the two nucleic acid fragments used in step i) of the method according to claim 6.

9. Nucleotide probe according to claim 8 comprising at least 20 consecutive bases of one of the following sequences J, K, L or M

J: 5'-CTGATCCGGCCACAGCCCGRCCCGCCGATC-3' SEQ ID NO: 9

K: 5'-AGGCGTCGGTGACAAAGGCCACGTA-GGCGA-3' SEQ ID NO: 10

L: 5'-CGAGGACCATGGAGGTGGCCATC-GTGGAAG-3' SEQ ID NO: 11

M: 5'-TGCCCTCATTGGCAACGTTTGCGCCCT-GCC-3 SEQ ID NO: 12

10. Nucleotide probe according to claim 8 included in a plasmid pMT02 including bases 309 to 1219 of the sequence IS 6110.

11. Kit for the detection of the presence of *Mycobacterium tuberculosis* in a biological sample comprising:

two of the nucleic acid fragments according to claim 1.

12. Isolated nucleic acid sequence, specific for *Mycobacterium tuberculosis* having the sequence:

```
             10         20         30         40         50         60
         GTCGACACGC CTTCTGCACG GGAAGTCCTT CTGCGGCCAT CGTTGCTATG GCCGCTTACT 70         80         90        100        110        120
         GCCTTCTAGT CCGTGCGGCT CTCGCAACAG CTCACGGGAC CTTTTTGAGG ATCGCCACTT 130        140        150        160        170        180
         CAGGTCTTCA ACTCGCGGAT GCCCTCATTG GCAACGTTTG CGCCCTGCCT TGGGGCGGCC 190        200        210        220        230        240
         GGCAGCCACC AAGTCGAGCA CTTTGCGGCG GAACTACTCG GGGTAACACT TCGGCACGGA 250        260        270        280        290        300
         CACGGCTCGT TCGACGGACG TCGTGACCAG AAGTCGAGCA AACCGACTCC ACTCTAGCTA 310        320        330        340        350        360
         GTGATACAAG CTTTTTTGTA GCCGCGCGAT GAACCGCCCC GGCATGTCCG GAGACTCCAG 370        380        390        400        410        420
         TTCTTGGAAA GGATGGGGTC ATGTCAGGTG GTTCATCGAG GAGGTACCCG CCGGAGCTGC 430        440        450        460        470        480
         GTGAGCGGGC GGTGCGGATG GTCGCAGAGA TCCGCGGTCA GCACGATTCG GAGTGGGCAG 490        500        510        520        530        540
         CGATCAGTGA GGTCGCCCGT CTACTTGGTG TTGGCTGCGC GGAGACGGTG CGTAAGTGGG 550        560        570        580        590        600
         TGCGCCAGGC GCAGGTCGAT GCCGGCGCAC GGCCCGGGAC CACGACCGAA GAATCCGCTG 610        620        630        640        650        660
         AGCTGAAGCG CTTAGCGGCG GGACAACGCC GAATTGCGAA GGGCGAACGC GATTTTAAAG 670        680        690        700        710        720
         ACCGCGTCGG CTTTCTTCGC GGCCGAGCTC GACCGGCCAG CACGCTAATT AACGGTTCAT 730        740        750        760        770        780
         CGCCGATCAT CAGGGCCACC GCGAGGGCCC CGATGGTTTG CGGTGGGGTG TCGAGTCGAT 790        800        810        820        830        840
         CTGCACACAG CTGACCGAGC TGGGTGTGCC GATCGCCCCA TCGACCTACT ACGACCACAT 850        860        870        880        890        900
         CAACCGGGAG CCCAGCCGCC GCGAGCTGCG CGATGGCGAA CTCAAGGAGC ACATCAGCCG 910        920        930        940        950        960
         CGTCCACGCC GCCAACTACG GTGTTTACGG TGCCCGCAAA GTGTGGCTAA CCCTGAACCG 970        980        990       1000       1010       1020
         TGAGGGCATC GAGGTGGCAA GATGCACCGT CGAACGGCTG ATGACCAAAC TCGGCCTGTC 1030       1040       1050       1060       1070       1080
         CGGGACCACC CGCGGCAAAG CCCGCAGGAC CACGATCGCT GATCCGGCCA CAGCCCGTCC 1090       1100       1110       1120       1130       1140
         GGCCGATCTC GTCCAGCGCC GCTTCGGACC ACCAGCACCT AACCGGCTGT GGGTAGCAGA 1150       1160       1170       1180       1190       1200
         CCTCACCTAT GTGTCGACCT GGGCAGGGTT CGCCTACGTG GCCTTTGTCA CCGACGCCTA 1210       1220       1230       1240       1250       1260
         CGCTCGCAGG ATCCTGGGCT GGCGGGTCGC TTCCACGATG GCCACCTCCA TGGTCCTCGA 1270       1280       1290       1300       1310       1320
         CGCGATCGAG CAAGCCATCT GGACCCGCCA ACAAGAAGGC GTACTCGACC TGAAAGACGT
```

-continued

```
        1330       1340       1350       1360       1370       1380
   TATCCACCAT ACGGATAGGG GATCTCAGTA CACATCGATC CGGTTCAGCG AGCGGCTCGC 1390       1400       1410       1420       1430       1440
   CGAGGCAGGC ATCCAACCGT CGGTCGGAGC GGTCGGAAGC TCCTATGACA ATGCACTAGC 1450       1460       1470       1480       1490       1500
   CGAGACGATC AACGGCCTAT ACAAGACCGA GCTGATCAAA CCCGGCAAGC CCTGGCGGTC 1510       1520       1530       1540       1550       1560
   CATCGAGGAT GTCGAGTTGG CCACCGCGCG CTGGGTCGAC TGGTTCAACC ATCGCCGCCT 1570       1580       1590       1600       1610       1620
   CTACCAGTAC TGCGGCGACG TCCCGCCGGT CGAACTCGAG GCTGCCTACT ACGCTCAACG 1630       1640       1650       1660       1670       1680
   CCAGAGACCA GCCGCCGGCT GAGGTCTCAG ATCAGAGAGT CTCCGGACTC ACCGGGCGG 1690       1700       1710       1720       1670       1740
   TTCACGATTG GGCCGCCGTA AGGAATGCGT CATGAGCGAC TTCGCATCAC GGGCGACCAA 1750       1760       1770       1770       1790       1800
   TCATTAATTT GTCAAACCCT TTGAGATGCA CTACTTGTCC ACATTTTGTA CACGAAATAC 1810       1820       1830       1840       1850       1850
   CTAACACACT ATGGTGCACA TCACGCACTT CCACGTTCCG TATTCGGTGT ACGATTTGTC 1860       1870
   ACGCAACTAA GCGTTCAAGA GGGAGT(SEQ ID NO: 15).
```

13. Method for detection of the presence of *Mycobacterium tuberculosis* according to claim 6 wherein, prior to step i) of claim 6 the DNA contained in the sample is extracted to make it accessible for hybridization.

14. Kit according to claim 11 further comprising a component making it possible to verify the sequence of the amplified fragment comprising the nucleotide probe according to claim 8.

15. Method for the detection of the presence of *Mycobacterium tuberculosis* according to claim 6 wherein said amplified DNA sequences are separated by means of gel electrophoresis and visualized.

16. Method for the detection of the presence of *Mycobacterium tuberculosis* according to claim 6 further comprising the step of verifying the sequence of the amplified fragment.

17. Method for the detection of the presence of *Mycobacterium tuberculosis* according to claim 18 wherein the sequence of the amplified fragment is verified by means of hybridization with a nucleotide probe according to claim 8, by sequencing or by analysis of restriction sites.

18. Kit according to claim 15 wherein said component is a nucleotide probe hybridizing with the amplification products resulting from a procedure for detection of the presence of *Mycobacterium tuberculosis* in a biological sample comprising the steps of:

i) placing the biological sample in contact with two isolated nucleic acid fragments comprising one of the sequences I, II, III and IV wherein I is a sequence selected from the group consisting of one of the sequences A to H:

A: 5'-CCCGCGGCAAAGCCCGCAGGACCAC-GATCG-3' SEQ ID NO: 1

B: 5'-CGACCCGCCAGCCCAGGATCCTGCGAGCGT-3' SEQ ID NO: 2

C: 5'-GGCGGGTCCAGATGGCTTGCTCGATCGCGT-3' SEQ ID NO: 3

D: 5'-GTTGGCGGGTCCAGATGGCTTGCTCGATCG-3' SEQ ID NO: 4

E: 5'-TCAAAGGGTTTGACAAATTMTGATTGGTC-3' SEQ ID NO: 5

F: 5'-TCGTGTACAAAATGTGGACAAGTA-3' SEQ ID NO: 6

G: 5'-TCGACGGACGTCGTGACCAGMGTC-3' SEQ ID NO: 7

H: 5'-GTCGACACGCCTTCTGCACGGGAAGTCCTT-3' SEQ ID NO: 8

II is a sequence including at least 10 consecutive bases of one of the sequences A to H and consisting of a total length of about 20 to 40 bases;

III is a sequence consisting of a length of 20 to 40 bases which hybridizes with sequence I or with sequence II; and IV is a sequence fully complementary to one of the sequences I, II or III;

ii) amplifying the DNA of *Mycobaterium tuberculosis*; and iii) visualizing the amplified DNA fragments corresponding to the fragment flanked by the nucleic acid fragments, said probe including a sequence having a length of at least 20 bases which hybridizes with the part of the sequence IS 6110 located between the two nucleic acid fragments used in step i) of the method according to claim 6.

* * * * *